USO05681259A

United States Patent [19]

August

[11] Patent Number: 5,681,259
[45] Date of Patent: Oct. 28, 1997

[54] METHOD AND APPARATUS FOR BIOPHILICALLY PROMOTING PATIENT RELAXATION, FOR REDUCING PHYSICAL AND/OR PSYCHOLOGICAL PATIENT STRESS AND FOR EXPEDITING PATIENT RECOVERY

[75] Inventor: Joseph August, Woodstock, N.Y.

[73] Assignee: Healing Environments International, Inc., Woodstock, N.Y.

[21] Appl. No.: 583,473

[22] Filed: Jan. 5, 1996

[51] Int. Cl.$^6$ .................................................. A61M 21/00
[52] U.S. Cl. ........................... 600/27; 600/26; 40/158.1; 160/10
[58] Field of Search .............................. 600/26, 27, 28; 40/158.1; 160/10

[56] References Cited

U.S. PATENT DOCUMENTS

| | | |
|---|---|---|
| 709,466 | 4/1902 | Butt . |
| 1,779,764 | 10/1930 | Dasch ........................................ 160/10 |
| 1,821,053 | 9/1931 | Diez et al. . |
| 2,206,281 | 7/1940 | Goeller . |
| 3,140,709 | 7/1964 | Weisz . |
| 3,643,941 | 2/1972 | Kashar . |
| 3,713,311 | 1/1973 | Oliver et al. . |
| 3,773,049 | 11/1973 | Babichev et al. . |
| 3,826,250 | 7/1974 | Adams . |
| 4,017,989 | 4/1977 | Murray . |
| 4,041,630 | 8/1977 | Holbrook . |
| 4,047,377 | 9/1977 | Banks, Jr. . |
| 4,082,918 | 4/1978 | Chang et al. . |
| 4,124,022 | 11/1978 | Gross . |
| 4,573,449 | 3/1986 | Warnke . |
| 4,640,267 | 2/1987 | Lawson . |
| 4,681,096 | 7/1987 | Cuervo . |
| 4,762,131 | 8/1988 | Okuda . |
| 4,763,428 | 8/1988 | Fischer ........................................ 40/712 |

(List continued on next page.)

OTHER PUBLICATIONS

Visual Therapy Concepts & Images by Joey Fischer, Art Research Institute Ltd. Atlanta, GA 30327 Nov. 1995 8 pages.
Visual Therapy Concepts & Images by Joey Fischer, Art Research Institute Ltd. Atlanta, GA 30327 Oct. 1995.
Kaplan et al. Rated Preference and Complexity for Natural & Urban Visual Material, Perception & Psychophysics, 1972, V. 12(4).

(List continued on next page.)

Primary Examiner—Jennifer Bahr
Assistant Examiner—Rosiland Kearney
Attorney, Agent, or Firm—Kuhn and Muller

[57] ABSTRACT

An apparatus that promotes patient relaxation, reduces patient stress, and/or expedites patient recovery, in a health care facility or home-based convalescent environment. The apparatus includes a substantially glare-free visual display device with one or more open, natural, serene and, preferably, savanna-like landscape pictures. Such pictures, including large size high resolution photo-realistic images, are displayed by means of a substantially glare-free display device, such as a flexible panel of fabric material positioned near a hospital bed or a like item of furniture, in close proximity to the patient so as to give the patient the perception of being in a natural and biophilic setting. In certain embodiments of the invention, the biophilic picture is removably attached to a movable wall, partition or hospital curtain structure which forms at least part of an enclosure substantially around at least part of the hospital bed. Such embodiments are designed to meet all relevant health care codes and standards in regard to fire retardancy and hygiene. The patient's experience of viewing the biophilic visual image may be enhanced by augmenting the visual installation with the playing of audio recordings of substantially natural sounds and/or providing a means to broadcast appropriate natural aromatic scents into the patient's immediate environment.

8 Claims, 8 Drawing Sheets

U.S. PATENT DOCUMENTS

| | | | |
|---|---|---|---|
| 5,125,175 | 6/1992 | Huff, Jr. | |
| 5,219,322 | 6/1993 | Weathers | 600/27 |
| 5,266,070 | 11/1993 | Hagiwara et al. | 600/27 |
| 5,267,942 | 12/1993 | Saperston | |
| 5,289,438 | 2/1994 | Gall | |
| 5,304,112 | 4/1994 | Mrklas et al. | 600/27 |
| 5,307,574 | 5/1994 | Huff, Jr. | |
| 5,356,368 | 10/1994 | Monroe | |
| 5,377,024 | 12/1994 | Dillinger | |
| 5,403,263 | 4/1995 | Rodgers | |
| 5,425,699 | 6/1995 | Spiegel | |
| 5,433,223 | 7/1995 | Moore-Ede et al. | |

OTHER PUBLICATIONS

R. S. Ulrich, Visual Landscapes & Psychological Well-Being Landscape Research, 4(!), 1979: 17–23.

R. S. Ulrich, Natural Versus Urban Scenes, Some Psychophysiological Effects. Environment & Behavior, vol. 13 No. 5 Sep. 1981 pp. 523–556 Sage Pub.

Moore et al A Prison Environment's Effect on Health Care Service Demands. J. Environmental Systems, vol. 11(1) 1981 Sage Pub.

R. S. Ulrich, Aesthetic & Affective Response to Natural Environment Behavior & the Natural Environment, NY: Plenum, 1983.

Behavior & the Natural Environment, Chaps. 1, 2, 4 Plenum Press, New York, 1983.

R. S. Ulrich, View Through A Window May Influence Recovery From Surgery, Science, vol. 224, pp. 420–421, Apr. 1984.

Schroeder et al Perception of Personal Safety in Urban Recreation Sites, Journal of Leisure Research 1984 vol. 16 No. 2, pp. 178–194.

M. West, Landscape Views & Stress Response in the Prison Environment, Thesis, Master of Landscape Architecture, 1986.

G. Orians, An Ecological & Evolutionary Approach to Landscape Aesthetics, Landscape Meaning and Values, London, 1986.

R. Ulrich, Effects of Hospital Environments on Patient Well-Being, Research Report from Dept. of Psychiatry & Behavioural Medicine, Univ. of Trondheim, Norway No. 55 vol. 9 1986.

R. Ulrich, Human Responses to Vegetation & Landscapes Landscape & Urban Plannin 13 (1986) 29–44 Elsevier Sci. Pub. Netherlan.

S. Verderber, Dimensions of Person-Window Transactions . . . Environment & Behavior, vol. 18 No. 4, Jul. 1986 450–466.

Verderber et al Windows, Views & Health Status . . . Journal of Architectural & Planning Research 4:2(1987) 120.

H. Schroeder, Environment, Behavior & Design Research on Urban Forests, Advances in Environment Behavior & Design Plenum Press, NY 1989.

R. Ulrich, Role of Trees in Human Well-Being & Health Proceedings of the 4th Urban Forestry Conf. DC 1990, pp. 25–30.

Ulrich et al Psychophysiological Indicators of Leisure Cons. Journal of Leisure Research, 1990, V. 22, No. 2, pp.154–166.

R. Ulrich, Effects of Healthcare Interior Design . . . Innovations in Healthcare Design, NY, Van Nos. Rein. 88–104, 1990.

Clearwater et al Functional Aesthetics to Enhance Well-Being in Isolated & Confined Settings, The Human Experience in Antarctica: Applications to life in Space, Springer-Verlag, New York 1990.

Coss et al. All that Glistens: Water Connotations in Surface Finishes, Ecological Psychology, 2(4), 367–380, 1990.

R. Parsons, Potential Influences of Environmental Perception on Human Health, Journal of Environ. Psych. (1991) 11 1–23.

Francis et al, Places People Take Their Problems, Environmental Design Research Assn., 22/1991 178–184.

Hartig et al Restorative Effects of Natural Environment Experiences, Environment & Behavior, v/ 23 #1, 1991, 3–26 Sage Pub.

Ulrich et al Stress Recovery During Exposure to Natural & Urban Environments, Journal of Environmental Psych. 1991 II, 201–230 Academic Press.

Sheets et al Affect, Cognition & Urban Vegetation: Some Effects of adding trees along city streets. Environment & Behavior vol. 23 No. 3, 1991 285–304 Sage Pub.

Orians et al Evolved Responses to Landscapes, The Adapted Mind, New York 1992 Oxford Univ. Press.

Ulrich et al Influences of Passive Experiences with Plants . . . The Role of Horticulture in Human Well-Being & Soc. Dev. 93–105 1992 Timber Press.

R. Ulrich, The Healing Environment—How Design impacts Wellness, Healthcare Forum Journal, 20 Sep./Oct. 1992.

Herzog et al Tranquility & Preference as Effective Qualities of Natural Environments, Journal of Environmental Psych.1992 12, 115–127.

Chokor et al An Assessment of Preference for Landscapes . . . Journal of Environmental Management (1992) 34, 237–256.

R. Ulrich, Biophilia, Biophobia & Natural Landscapes The Biophilia Hupothesis, 1993 DC Island Press Chap. 3.

Nasar et al Proximate Physical Cures to Fear of Crime Landscape & Urban Planning, 26 1993) 161–178 Elevier Sci. Pub. Amsterdam.

Program Abstracts, Psychophysiology, vol. 30, Aug. 1993 Supplement 1, Germany.

R. Parsons, Conflict Between Ecological Sustainability and Environmental Aesthetics: Conundrum, Canard or Curiosity, Landscape and Urban Planning v. 32 (1995) 227–244.

E. P. Odum, Fundamental of Ecology, 3rd Ed. 1971 W. B. Saunders Co. PA.

E. L. Shafer, Jr. & T. A. Richards, A Comparison of Viewer Ractions to Ourdoor Scenes & Photographs of Those Scenes, USDA Forest Service Research Paper NE-302, 1974.

Stephen R. Kellert & Edward O. Wilson, The Biophilia Hypothesis, Island Press, Shearwater Books, Wash. DC 1993.

E. O. Wilson, Biophilia, Harvard Univ. Press, 1984.

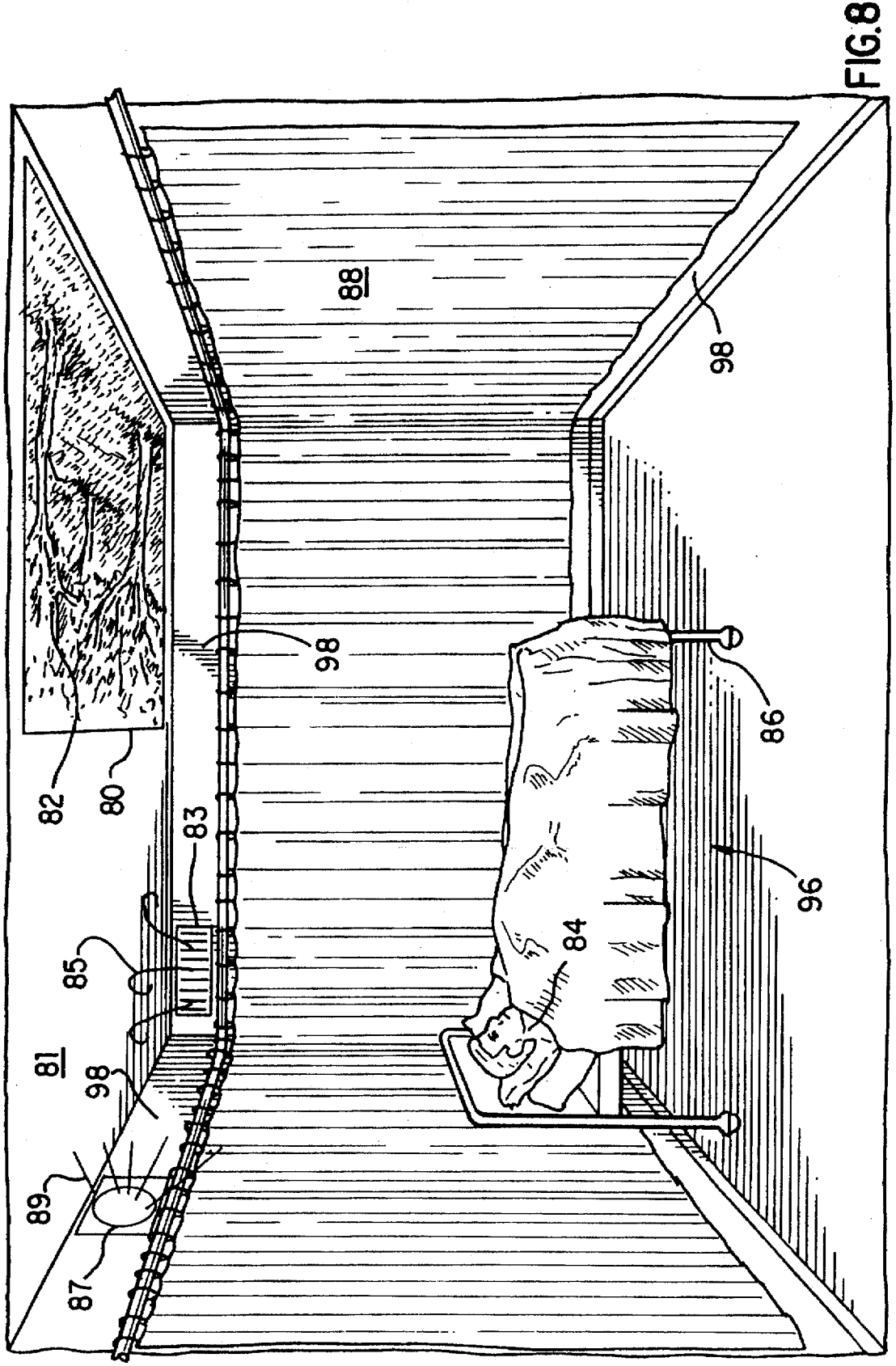

METHOD AND APPARATUS FOR BIOPHILICALLY PROMOTING PATIENT RELAXATION, FOR REDUCING PHYSICAL AND/OR PSYCHOLOGICAL PATIENT STRESS AND FOR EXPEDITING PATIENT RECOVERY

FIELD OF THE INVENTION

The present invention relates generally to the field of methods and devices for promoting patient recovery; more particularly, the present invention concerns methods and apparatuses used to expose patients to appropriately selected visual stimuli which promote patient recovery in intimate settings in hospital room environments and like settings.

BACKGROUND OF THE INVENTION

Positive psychological and physiological responses are elicited in humans by visual exposure to pleasing landscape images such as pictures of spatially open natural landscapes. (Roger S. Ulrich, 1993, "Biophilia, Biophobia and Natural Landscapes", Chapter 3, pages 73–137, in: Stephen R. Kellert and Edward O. Wilson editors, *The Biophilia Hypothesis*, Island Press, Washington, D.C.). The preferred landscape image is a savanna-type landscape. By definition, a savanna-type landscape is a "grassland with scattered trees or scattered clumps of trees, a type of community intermediate between grassland and forest" (Eugene P. Odum, 1971, *Fundamentals of Ecology, Third Edition*, W. B. Saunders Company, Philadelphia, Pa.).

In one of his seminal and theoretical works, renowned evolutionary biologist Edward O. Wilson (1984), *Biophilia: The Human Bond with Other Species*, Harvard University Press, Cambridge, Mass.) suggests that humans are genetically predisposed to respond positively (biophilically) to savanna-like landscapes. After the publication of Wilson's seminal work on island biogeography (Robert H. MacArthur and Edward O. Wilson, 1967, *The Theory of Island Biogeography*, Princeton University Press, Princeton, N.J.) and his expansive synthesis on sociobiology (Edward O. Wilson, 1975, *Sociobiology: The New Synthesis*, Harvard University Press, Cambridge, Mass.), biologists and others wrote many papers, dissertations and books on these topics of modern bioscience. Like the responses by the bioscientific community to his 1967 and 1975 works, Wilson's 1984 publication of *Biophilia: The Human Bond with Other Species* has prompted the writing of many scientific papers by a wide diversity of authorities. Among these works on biophilia are two papers especially relevant to the present invention: the aforecited "Biophilia, Biophobia and Natural Landscapes" by Ulrich, and "Humans, Habitats, and Aesthetics" by Judith H. Heerwagen and Gordon H. Orians (*1993*, Chapter 4, pages 138–172, in Stephen R. Kellert and Edward O. Wilson, editors, *The Biophilia Hypothesis*, Island Press, Washington, D.C.).

The biophilic theory of Wilson supports the belief that natural selection favored the survival of paleohominids (ancestors of modern humans, *Homo sapiens*) genetically predisposed to inhabiting landscapes dominated by plant life forming vegetation having a physiognomy of a savanna. Such ancestral hominids are viewed as having innate aversions to desert, densely forested and like landscapes generally less favorable to paleohominid survival than savannas. Human evolution is believed to have occurred substantially within tropical savannas in Africa. Predation, food-availability and other selection pressures were generally more favorable to human survival and evolution within these tropical savannas than in other kinds of African landscapes (such as tropical rain forest, mountainous, desert and like environments). Selection promoted disproportionately high survival of hominids and hominid genes favoring savanna-oriented behaviors. As evolution proceeded, there was a build-up and strengthening of genes and gene-combinations further predisposing hominid populations to savanna conditions. Wilson believes that these innate savanna-oriented characteristics continue in populations of modern humans and that modern humans are biophilically predisposed to responding favorably to savanna or savanna-like conditions. Certain embodiments of the present invention are in accord with this belief of one of the most widely respected and acclaimed biologists in the world today.

In the aforementioned 1993 publication of Ulrich, Ulrich reports evidence that simulations (including color photographs) of natural environments elicit restorative and other positive responses from human viewers and suggests that such simulations may serve as at least partial substitutes for real nature in terms of eliciting short-term restorative responses. Other scientific authorities are mentioned by Ulrich as providing proof that the viewing of natural settings positively affects the viewer by reducing stress (confirmed by such central nervous system indicators as blood pressure). This reporting by Ulrich is consistent with the innate biophilic landscape affinity believed by Wilson to characterize modern humans. The work of Ulrich suggests that positive (biophilic) responses can be elicited from patients within a very short time after patient exposure to wall art showing spatially open serene natural settings.

However, most attempts to reduce stress in a hospital or therapeutic setting have been sound-oriented, wherein music or other sounds are electronically delivered to a patient. Where visual images are used to address patient well being, the images are either displayed remotely in a far away picture frame, or in optically glare-producing video screens.

Among the earlier background art patents related to methods of patient recovery are the following:

| U.S. Pat. No. | Inventor | U.S. Pat. No. | Inventor |
|---|---|---|---|
| 3,140,709 | Weisz | 4,681,096 | Cuervo |
| 3,643,941 | Kashar | 4,762,131 | Okuda |
| 3,773,049 | Rabichev et al. | 4,763,428 | Fischer |
| 3,826,250 | Adams | 5,267,942 | Saperston |
| 4,047,377 | Banks | 5,289,438 | Gall |
| 4,082,918 | Chang et al. | 5,352,181 | Davis |
| 4,124,022 | Gross | 5,356,368 | Monroe et al |
| 4,553,534 | Stiegler | 5,377,024 | Dillinger |
| 4,573,449 | Warnke | 5,403,263 | Rodgers |
| 4,640,267 | Lawson | 5,425,699 | Spiegel |
| | | 5,433,223 | Moore |

The most relevant patents are U.S. Pat. No. 5,403,263 of Rodgers, for a method of reducing the recovery time and stress associated with surgery and U.S. Pat. No. 4,763,428 of Fischer for providing a nature scene in a hospital wall-mounted picture frame. Rodgers '263 describes a method to reduce hospital recovery time and stress by providing verbal voice-over suggestions and soothing anxiolytic music before, during and after surgery. Fischer '428 describes the use of wall mounted pictures to assist in patient healing, but does not focus on what pictures to select other than nature scenes in general.

Weisz (U.S. Pat. No. 3,140,709) describes a pain relieving apparatus wherein acoustical sounds such as music are fed through ear phones to divert a patient's attention from pain.

Rabichev et al. (U.S. Pat. No. 3,773,049) describe an electronic apparatus for treating neuropsychic and somatic disorders with repetitive exposure of the patient to light, heat and sound radiation sources.

Banks (U.S. Pat. No. 4,047,377) discloses an electronic sleep promotion apparatus wherein a wide band audio frequency generator applies audio impulses to a person.

Chang et al. (U.S. Pat. No. 4,082,918) describe an electronic audio device which provides analgesic sounds to dental patients.

Gross (U.S. Pat. No. 4,124,022) describes an electronic audio speaker in the shape of a heart, which provides repetitive slow heartbeat sounds, to relax a person.

Kashar (U.S. Pat. No. 3,643,941) describes a relaxation chamber containing a plurality of Styrofoam® balls to simulate movement of a person within a swimming pool. Colored lights are projected upon the Styrofoam® balls to enhance the person's relaxation.

Adams (U.S. Pat. No. 3,826,250) discloses a relaxation chamber including a lounge chair wherein lights and sounds are electronically provided to a resting person.

Steigler (U.S. Pat. No. 4,553,534) describes a stress-reducing helmet with an eye shield, wherein electronic images and sounds are transmitted to the wearer.

Warnke (U.S. Pat. No. 4,573,449) describes a method for sleep enhancement and/or relaxation wherein a headphone generates electronic sound pulses, which are provided to an insomniac person to induce sleep.

Lawson (U.S. Pat. No. 4,640,267) and Cuervo (U.S. Pat. No. 4,681,096) both describe methods and associated devices to abate an infant's crying, wherein electronic sounds or vibrations are scheduled for repetitive introduction to the infant.

Gall (U.S. Pat. No. 5,289,438) discloses a consciousness-altering apparatus for persons, wherein multiple sound stimuli are electronically provided to a person.

Monroe (U.S. Pat. No. 5,356,368) describes a method and apparatus for altering consciousness and inducing sleep by measuring electroencephalogram (EEG) brain wave forms of a person during sleep or relaxation, and using sounds to try and reproduce the sleep inducing or relaxation-inducing brain waves of the person.

Dillinger (U.S. Pat. No. 5,377,024) describes an electronic color forming image construction device.

Spiegel (U.S. Pat. No. 5,425,699) describes the use of electronically produced sound waves to induce hypnosis in a person.

Okuda (U.S. Pat. No. 4,762,131) discloses an electronic nerve stimulation including lights and sounds to treat paralytic patients.

Monroe et al. (U.S. Pat. No. 5,356,368) describe a method for predicting when a night-shift worker might lose alertness.

Saperston (U.S. Pat. No. 5,267,942) discloses the use of electronically generated sounds to monitor optimal target heart rates in persons.

Davis (U.S. Pat. No. 5,352,181) describes a method and apparatus for inducing relaxation by providing verbal and musical sounds in ascending and descending crescendos and phases, to stimulate relaxing alpha and beta brain waves.

However, Rodgers '263 and most of the above noted background art patents are directed to electronic sound generating devices to induce relaxation states in users. Some of these devices, such as the embodiments of Okuda '131 and Kashar '941, involve the use of electronically generated flashing lights to induce relaxing states of mind.

Furthermore, providing such a repetitive exposure of a patient to music, sounds and/or flashing lights has the disadvantage of being expensive to install and also may overstimulate the patient.

Moreover, these background art devices do not describe a method and apparatus for providing biophilic landscape images to hospital patients to promote recovery.

Furthermore, the hospital room environment itself has the disadvantage of discouraging exposure of persons to pictures in general, because slidable fabric curtains are often drawn around the patient's bed, thereby hiding any wall-mounted pictures, such as described in U.S. Pat. No. 4,763,428 of Fisher, from the patient's view.

Fischer also discloses in an unpatented publication entitled "Visual Therapy" the displaying of one of many nature photography scenes in a light box or a lighted electronic video screen in a health care setting. However, the lighted images are subject to optical glare.

The background art of Fischer '428 and the Fischer "Visual Therapy" publication of visually oriented approaches to patient well being is aimed primarily at providing either a reusable lockable means, such as a picture frame, or a light box or video screen, to display pictures that are only generally described as "having a therapeutic value", and "particularly well suited to visually involve, distract and occupy the attention of the viewer" of nature photography on the hospital room wall. There is no specificity as to the theoretical basis for selection of the nature photography; nor are any selection guidelines presented.

While a hospital curtain exhibits a large, convenient surface upon which to display pictures, curtains have not been generally used to display framed pictures, because the weight of a picture frame may distort the curtain and/or because the rigid picture frame may be a hazardous hindrance obstructing egress in the vicinity of the curtain. In addition, light boxes and lighted video screens present other electricity related hazards.

Therefore, there is a need for a lightweight, flexible display means for pictures, which can be attached to a hospital curtain without distorting the curtain and without obstructing egress to the patient in the vicinity of the curtain.

In fact, flexible removable pictures have mainly been provided within infant cribs to protect an infant's safety, as noted in U.S. Pat. Nos. 5,307,574 and 5,125,175 of Huff.

Moreover, imprinted photographic pictures cannot normally be displayed on fabrics, such as curtains, because the images fade with repeated washing of the fabric materials.

The technical challenges in providing such cubicle curtain-mounted images include (1): Any fabric that is used must either be inherently fire retardant or specially topically treated to meet the fire retardancy standards as set forth in National Fire Protection Association (i.e., NFPA) Code 701. (2) The printing must produce images of sufficient high-resolution photo-realism and sufficient size (e.g., four by five feet) to give the patient the perception of actually being in a natural (i.e., biophilic-like) setting. (3) The photo-realistic image must be printed on inherently fire retardant or treated fabric, in a manner that upholds the post-printing fire retardancy of the fabric and in a manner that enables the fabric to be laundered and disinfected at the high water and drying temperatures required by hospital sanitary codes and standards while maintaining the image quality of the picture.

High resolution, non-fading printing of photographic images on cloth fabrics may be obtained by special printing processes, such as, for example, sublimation printing. Sublimation printing produces images which have high image resolution with much clarity and brilliance, without the visually disturbing effects of glare produced by light boxes or electronic screens, such as described in the Fischer "Visual Therapy" publication.

Among the background art describing sublimation printing include U.S. Pat. Nos. 5,460,871 of Andersen, 5,441,997 of Walsh, 5,389,493 of Asai, 5,329,381 of Payne, 4,997,506 of Recher, and 4,804,977 of Long.

In sublimation printing, the coloring agents are subliminally transferred to the fabric. Sublimation printers use sublimation powders or printer ribbons to produce heat transfers, which release sublimation inks in a wide variety of distinctive colors, as noted in U.S. Pat. No. 5,281,499 of Bussard.

Since the resolution quality is achieved with photographic images printed on fabrics by sublimation printing, the fabrics can therefore be fire retardant and washable, so that the fabrics can be laundered and disinfected when washed at high water temperatures with cleaning products.

Reusable fabrics are also much easier to clean and maintain than complicated light boxes or electronic video screens, and are more easily interchangeable than heavy, wall mounted picture frames.

Therefore, the high water temperatures and cleaning products (which are needed to bring fabrics up to hospital and other sanitary codes,) do not substantially diminish the high resolution and clarity of photographic images produced by sublimation printing upon a fabric, such as hospital curtain material or another suitable fabric attachable to a hospital curtain. Moreover, these cleaning methods do not diminish the fire retardancy of the inherently fire retardant fabric.

OBJECTS OF THE INVENTION

Accordingly, an object of the present invention is to provide a method for visually and biophilically promoting patient relaxation, before, during and/or after medical procedures, such as surgery or diagnostic testing.

It is also an object of the invention is to provide a method for visually and biophilically reducing physical and/or psychological stress, promoting patient relaxation and expediting recovery in a patient before, during and/or after surgical or medical procedures in a hospital, medical or convalescent setting.

Another object of the invention is to provide a method for visually and biophilically expediting recovery of a medical and/or surgical patient.

A further object of the invention is to provide a method for visually and biophilically promoting surgical patient welfare in a hospital, medical or convalescent setting, or a like environment.

A still further object of the invention is to provide a method for visually exposing a patient to biophilic savanna-like scenes as biophilic stimuli before, during and/or after surgery and other medical procedures to promote relaxation, reduce patient stress and expedite patient recovery.

A yet further object of the invention is to provide a method which supplements visual biophilic stimuli with sound, aromatic and/or other stimuli for promoting medical patient relaxation, reducing patient stress and expediting patient recovery.

It is yet also an object of the present invention to provide a convenient changeable visual display means for displaying one or more biophilic pictures for which a predetermined patient has a biophilic affinity, in a facility associated with performance of diagnostic, treatment or surgical procedures, or in rehabilitation and convalescent settings.

It is a further object to provide such a visual display means to visually expose a patient to one or more biophilic pictures before, and/or after performance of surgery or other procedures on the patient.

It is also an object to provide a means for patient choice in selecting a visual display; such choice promotes the patient's self-efficacy, which thereby reduces stress and which promotes health and well being.

It is yet a further object to provide a patient with a visual display means with one or more biophilic pictures as biophilic stimuli for promoting patient relaxation, for reducing physical and/or psychological patient stress, and for expediting patient recovery time.

It is yet another object of the present invention to augment the foregoing visual exposure of patients to biophilic scenes by providing sound recordings conducive to causing patient relaxation.

It is a further object of the present invention to further augment the foregoing visual exposure of patients to biophilic scenes by also providing therapeutic aromatic materials to the patient.

It is yet another object to provide a method of promoting patient recovery while the patient is in a hospital bed by displaying the biophilic pictures on a structural surface such as a vertically draped curtain substantially near the bed, wherein the picture is positioned to allow the patient to readily and comfortably view the biophilic picture.

It is yet another object to improve over the disadvantages of the background art directed toward complicated electronic sound-oriented relaxation devices for surgical, medical and other patients.

It is yet another object to improve over the disadvantages of the background art directed toward expensive, optical glare-producing lighted electronic screen displays of pictures.

SUMMARY OF THE INVENTION

In keeping with these objects and others which may become apparent, the present invention provides a method of relaxing a patient in a health care, hospital or convalescent setting, by providing a patient with a choice of selecting for viewing one or more high resolution spatially open, serene natural landscape scenes to which the patient is believed to have an innate positive (biophilic) affinity, upon a fabric frame display member mounted upon a flexible wall partition, such as a hospital curtain. In one embodiment, the spatially open, serene natural landscape scene is a savanna-type landscape or a like scene to which humans are believed to have a biophilic affinity.

A biophilic landscape picture of the present invention is printed preferably on a flexible fabric by a high resolution sublimation printing process, wherein an image is first scanned into a computer and then transformed by state-of-the-art technology to the fabric, such as described in the "Background of the Invention" herein. The image may also be printed directly on all or a portion of a hospital curtain itself.

Because of hospital safety protocol and safety codes (such as what is referred to as "National Fire Protection Association (NFPA) 701" codes), the fabric must either be inherently flame retardant or specially treated to meet protocol or code requirements.

Moreover, in accord with hospital sanitary protocol, the fabric sheet pieces and inks thereon should be washable and durable to heated washing standards of 160° F. so that any infectious organisms thereon are eradicated.

The printing produces substantially glare-free photorealistic images of sufficient size (e.g. four by five feet) to give the patient the perception of actually being in a natural (i.e., biophilic) setting. Printing the photorealistic image is accomplished on inherently fire retardant or treated fabric in a manner that upholds the post-printing fire retardancy of the fabric and that enables the fabric to be laundered and disinfected at the required high water and drying temperatures required by hospital sanitary codes and standards without substantially degrading the image quality of the picture.

On a reverse side of the fabric one or more fastening means, such as strips of hook-and-loop-type fasteners, sold under the trade name of VELCRO®, are attached. Corresponding strips of hook-and-loop type fasteners are attached to a portion of a hospital room curtain which at least partly encloses a hospital patient's bed. Other conventional fasteners such as snaps, safety pins, clips, etc., may be substituted or additionally employed.

By attaching the fabric picture to the patient-facing side of the hospital curtain, the biophilic landscape picture can remain visible to the targeted patient in the bed even when the curtain is contracted.

During visiting hours, when the curtain is normally partially expanded, the landscape picture can be left visible on a portion of the curtain.

Preferably, the picture should be attached so that it is visible at the foot of the patient's bed, within the patient's line of vision.

In conjunction with exposure of the patient to the spatially open, serene natural landscape picture, the patient may be provided with soothing natural sounds appropriate to the landscape picture and/or mild aromatic odors reminiscent of natural aromas associated with the landscape picture.

In selecting a spatially open, serene natural landscape for the patient to view, it is important that the patient not be exposed to over-exciting or anxiety producing landscape scenes, (which may unconsciously raise the stress level of the patient and/or may affect the visual and auditory nerve balance mechanisms of the patient). Therefore, selection of the biophilic visual image to be conveyed to the patient preferably encompasses selection of spatially open, serene landscape scenes which are substantially the same as, or similar to, the archetypal savanna-typ.e landscape scenes, suggested by Ulrich, Wilson and other scientific authorities on biophilia.

The subjects of a biophilic scene, or other spatially open, serene, natural landscapes must be carefully chosen and the natural scenes should be selected in relation to the most recent relevant environmental psychology research (such as defined by Ulrich). Although pre-dating both the 1984 seminal work by Wilson and the subsequent 1993 publication of Ulrich, an example of environmental psychology methodology research on differential human perceptions of varying outdoor scenes is the 1974 work of Shafer and Richards entitled "A Comparison of Viewer Reactions to Outdoor Scenes and Photographs of These Scenes", (Shafer et al., 1974, *U.S. Dept. of Agriculture, Forest Service Research Paper No. NE*-302, Northeastern Forest Experiment Station, Forest Service, U.S.D.A., Upper Darby, Pa.)

In the Shafer and Richards study, eight different types of outdoor scenes were shown to viewers in three different modes: (i) on-site viewing of the actual scenes; (ii) viewing color transparencies of the scenes; and (iii) viewing color photographic prints of the scenes. Viewer responses to each scene were compared statistically and geographically to determine which outdoor scenes had more positive effects on the viewers.

Upon selection of the picture to be displayed to the patient, it should be conveniently displayed, such as on the hospital curtain, as noted before.

However, other embodiments of the present invention include other visual display means not previously described in this application. One such other kind of embodiment is a wall or ceiling mountable, roll-up-able and roll-down-able screen depicting a spatially open, serene natural landscape scene (preferably a biophilic savanna-type scene).

Unlike the generalized nature photography described in Fischer '428 and the Fischer "Visual Therapy" publication, the present invention applies the latest research findings and theory in the behavioral and natural sciences to the selection and installation of appropriate nature photography scenes in hospital rooms and other convalescent settings. It does so in a manner that creates a simulated natural environment to promote the hospitalized patient's recovery.

The selection of healing and recovery-promoting natural landscape scenes requires knowledge of the latest research findings concerning the health effects of viewing biophilic nature scenes, since not all natural landscape scenes have a therapeutic affect. In fact, uninformed, improper or inappropriate picture selection has been shown to have deleterious effects on patients, disturbing them rather than promoting their healing.

What is essential in the selection process is that the visual stimuli not merely tend to "involve, distract and occupy the attention of the viewer" but that such elicited patient responses promote the patient's healing and recovery. The present invention reflects an understanding of how to stimulate such viewer-based recovery responses because it is based on a firm foundation of the latest research findings and theoretical research focusing on the biophilic effects of viewing nature on human health outcomes. This research, by Wilson, Heerwagen, Orians, and Ulrich et al informs the user of the appropriate method of selection of recovery-promoting biophilic natural landscape scenes.

Merely placing a picture on a hospital room wall whether in a frame, a light box or a video screen, is not sufficient to promote patient recovery. The Fischer '428 background art on hospital room walls is located at too remote a distance from the patient to promote the patient's perception of being in the environment represented by the picture. Moreover, while the Fischer "Visual Therapy" publication describes the lighted depiction of large photographs from light boxes or video screens, the light emitking features of the light boxes or video screens may produce unwanted optical glare.

Furthermore, viewing of wall mounted light boxes and video screens can be obstructed by fabric hospital curtains drawn between a patient and a hospital room wall.

Therefore, one embodiment of the present invention is distinguished from the background art by providing very large sized high resolution photo realistic biophilic natural landscape scenes that, by being printed on flexible fabric, enable these scenes to be removably mounted on the patient's bedside cubicle privacy curtain in the patient's direct line-of-sight at the foot of the bed, thereby providing the patient with an immediately close-up simulated natural visual environment.

Since wall-mounted art described in the background art has the disadvantage of being obscured from the patient's view whenever the cubicle curtain is drawn to provide privacy to the patient, the patient is therefore caused to have to choose to either have personal privacy or to be able to view the wall-mounted photography.

With the above-described embodiment of the current invention, the patient no longer has to suffer the above described dilemma. It provides the patient with an opportunity to choose one or more preselected biophilic scenes that, by virtue of their placement on the cubicle curtain, can be viewed at the discretion of the patient any hour of the day or night without the glare of a video screen or the remoteness of a wall mounted frame. With the embodiment of the present invention the patient is not forced to choose between having personal privacy or viewing wall-mounted nature photography.

On the contrary, with this embodiment of the present invention the patient is able to enjoy the benefit of (or exercise the choice of having) personal privacy while simultaneously having the opportunity to view selected restorative biophilic nature photography.

An additional embodiment of the latter-described embodiment augments the visual dimension of the environment with complementary audio recordings of biophilic sounds appropriate and specific to each scene. Still another embodiment augments the visual and audio stimuli with aromatic scents that are appropriate and specific to each scene.

Also, the method of the present invention may allow (after a set of spatially open serene natural landscape scenes is selected by the patient's care giver) the patient to select one or more of these scenes. This alternative variation permits patients to exercise choice, thereby improving the patient's self-efficacy and ultimate recovery.

Moreover, the biophilic or other spatially open, natural serene landscape scenes may be visually displayed substantially glare-free in other medical or convalescent environments, such as in the offices of health practitioners, (e.g., physicians, dentists, acupuncturists, chiropractors, and physical therapists). Other appropriate settings include diagnostic rooms at hospitals, adult day care centers, other institutional settings and/or at a private residence (such as where an infirm person might be confined to a particular room for extending periods of time while recovering from illness or surgery).

DESCRIPTION OF THE DRAWINGS

The present invention can best be understood in conjunction with the accompanying drawings, in which:

FIG. 8 is a perspective view of a further alternate embodiment of the present invention, showing a ceiling mounted-biophilic landscape image.

DETAILED DESCRIPTION OF THE PREFERRED EMBODIMENTS

Figure 1:
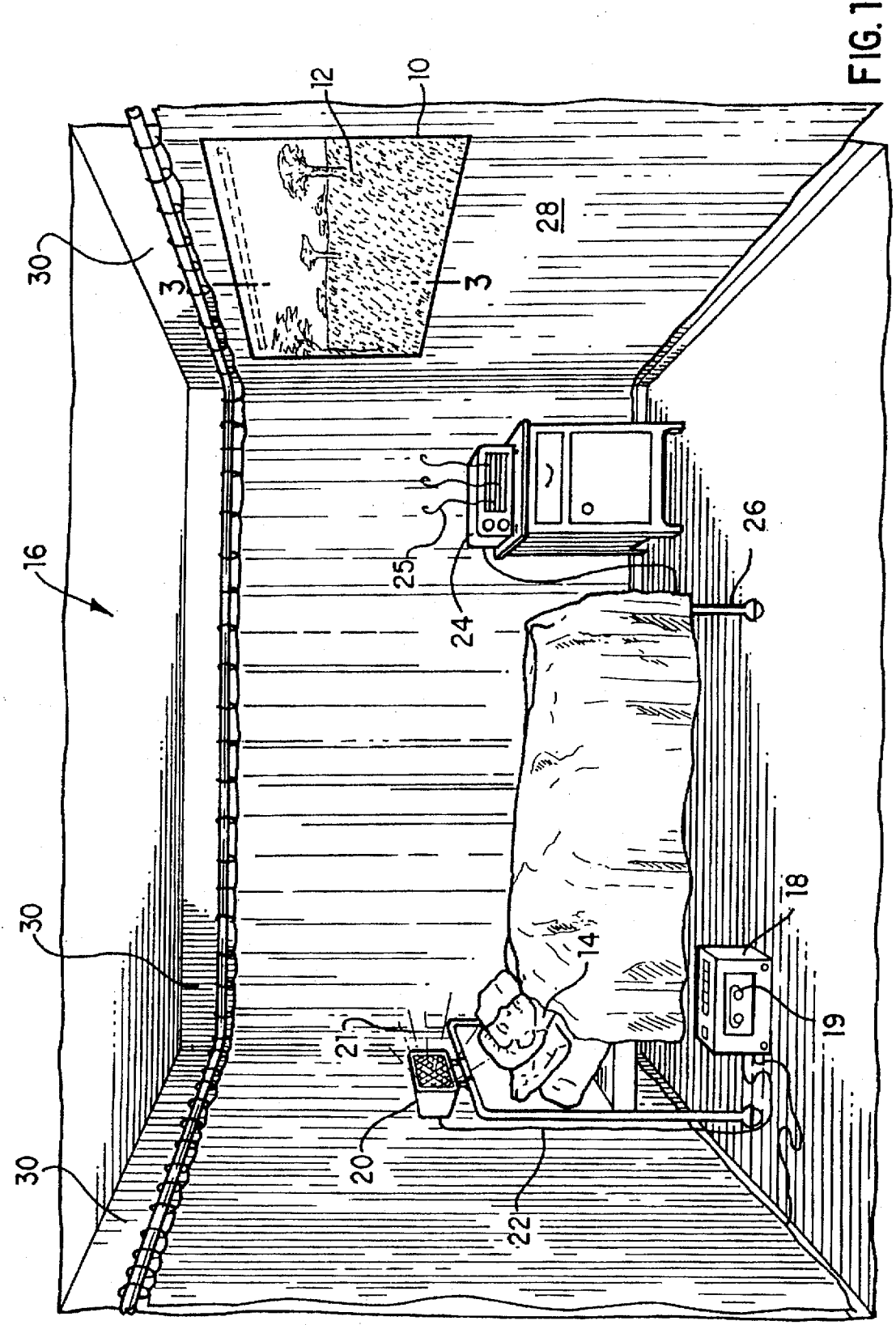
FIG. 1 is a perspective view of a hospital room setting of a preferred embodiment of the method of biophilically enhancing patient welfare.

FIGS. 1–8 depict a method and apparatus for promoting patient relaxation, for reducing physical and/or psychological patient stress, and/or for expediting patient recovery, before, during and/or after medical procedures, such as surgery.

The preferred method includes the steps of providing a changeable visual display device 10, 40, 50, 70 or 80 for displaying one or more appropriately selected spatially open, serene natural landscape pictures 12, 42, 52, 72 or 82 for which a predetermined patient, such as predetermined patient 14, 74 or 84, has a predisposed affinity.

Preferably, a biophilic picture such as picture 12, 42 or 72 is utilized. Other spatially open, serene natural landscape pictures, with specific landscape physiognomy criteria, such as picture 52 may also be used.

In FIG. 1, changeable visual display device 10 is provided in a facility associated with performance of surgical procedures, such as hospital room 16 having walls 30. Changeable visual display device 10 is used to visually expose predetermined patient 14 to one or more appropriately selected spatially open natural landscape pictures, such as biophilic picture 12, printed on display device 10, which display device 10 is substantially optically glare-free and removably attachable to a structure, such as hospital curtain 28, before, during and/or after performance of surgery or other medical procedures on patient 14.

Figure 7:
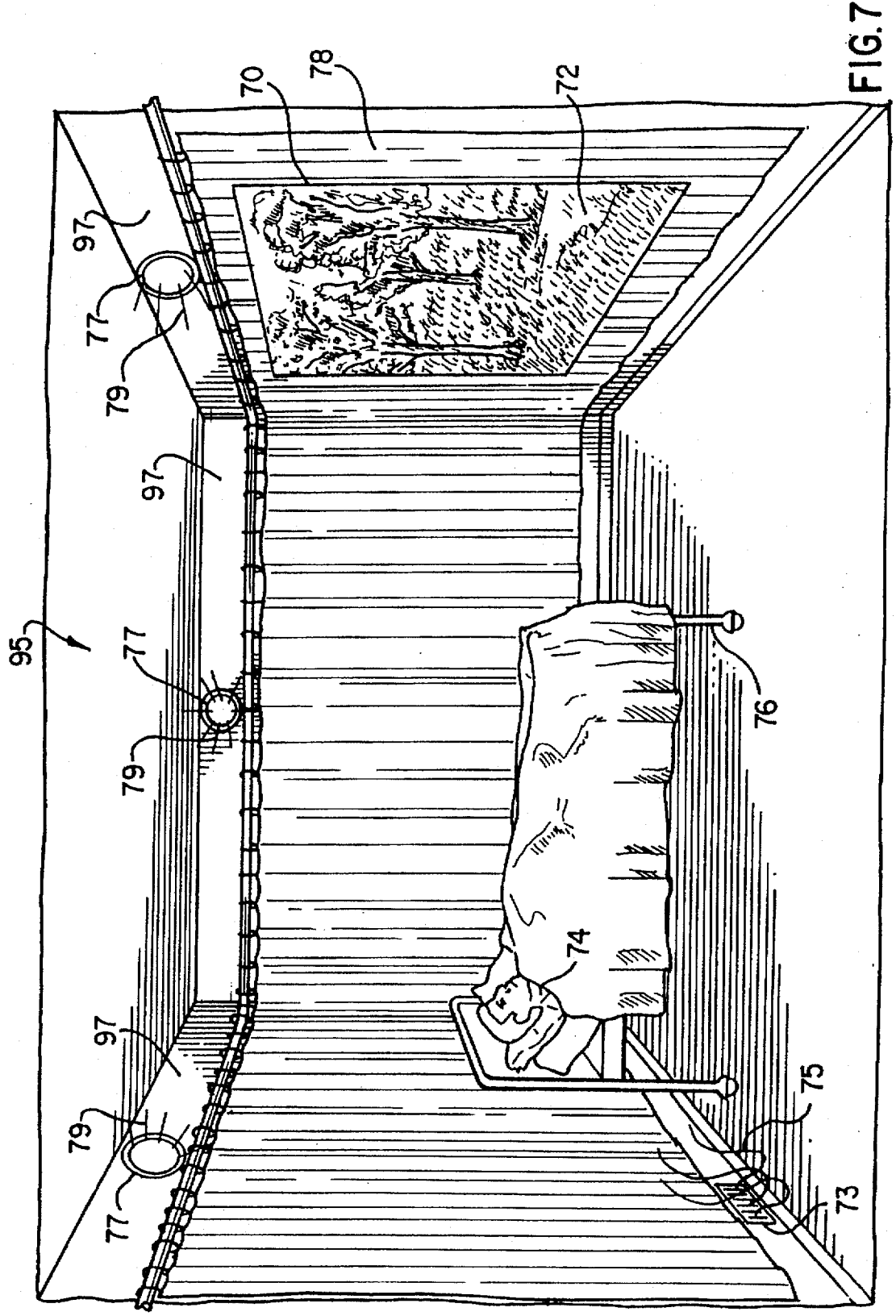
FIG. 7 is a perspective view of a hospital room setting of another embodiment of the present invention, showing a larger biophilic landscape image on a flexible fabric display.

Alternatively, as shown in FIG. 7, the visual display 70 of biophilic picture 72 may be large, such as four feet in height by five feet in width or larger, and may take up a substantial portion of viewing portion of hospital curtain 78 in room 95, so that patient 74 may concentrate on viewing biophilic image 72 without eyestrain produced by distant wall-mounted pictures or large, glare producing lighted images from light boxes or other electronic video screens. Moreover, the entire curtain may have a biophilic picture printed directly thereon.

As shown in FIG. 8, for patients who are immobilized in a substantially supine position, instead of upon curtain 88, biophilic image 82 upon display 80 may be provided upon the ceiling of room 96.

As respectively shown in FIGS. 1, 7 and 8, patient 14, 74 or 84 is visually exposed to at least one visual picture, such as biophilic image 12, 72 or 82 upon visually proximate and substantially glare-free display device 10, 70 or 80, as biophilic stimuli for neurologically and biophilically promoting in patient 14, 74 or 84 the sequelae effects of relaxation, reduction of physical and/or psychological stress, and/or acceleration of patient recovery time.

Additionally and synergistically, recordings of sounds conducive to causing patient relaxation, such as audio cassette tape 19, (or a compact disc) may be played on audio player device 18, which preferably is a device of the type including audio tape players and compact disc players, through speaker 20, such as amplified speakers, headphone or pillow speakers. Speaker 20 is connected to audio player device 18 by audio-signal-transmitting cable 22, or by suitable wireless communication means or other means, for producing sounds 21.

Playing the sound recordings on audio player device 18 causes the sounds 21 to be heard by patient 14 and augments patient 14's exposure to biophilic image 12 of display 10, thereby contributing to biophilic relaxation and ultimate recovery of patient 14. The recorded sounds preferably are natural sounds appropriate to the content of biophilic picture 12. Alternately, audible or subliminal healing promoting verbal suggestions or electronic sounds may be provided in conjunction with the viewing of the subject matter of biophilic picture 12 upon flexible display 10 mounted to curtain 28 or other suitable mounting means.

FIGS. 7 and 8 respectively show sounds 79 or 89 entering hospital rooms 95 and 96 through speakers 77 or 87 upon respective walls 97 or 98, from remotely located audio player devices.

As shown in FIG. 1, further additionally and synergistically therapeutic aromatic vapors 25 may be optionally emitted from aromatic vapor dispenser 24 so as to argument the positive effect of viewing of biophilic picture 12 by patient 14. Alternatively as shown in FIGS. 7 and 8, respective aromatic vapors 75 and 85 may be emitted through respective vents 73 and 83 from sites remote from respective rooms 95 and 96.

Visual display device 10, which contains biophilic picture 12, is removably mounted on a structural surface, such as hospital curtain 28, substantially near patient 14 in bed 26 in hospital room 16. Biophilic picture 12 is strategically situated in hospital room 16 so that patient 14 can comfortably view biophilic picture 12 substantially without distraction and in an substantially glare-free environment. The presence of hospital curtain 28 helps prevent or reduce such distraction from nonbiophilic visual sources, such as hospital room wall 30, or from lighted, optically glare-producing light boxes or video screens.

Moreover, additional biophilic pictures may be provided on other viewable portions of curtain 28, such as to the left or right side of patient 14.

Figure 2:
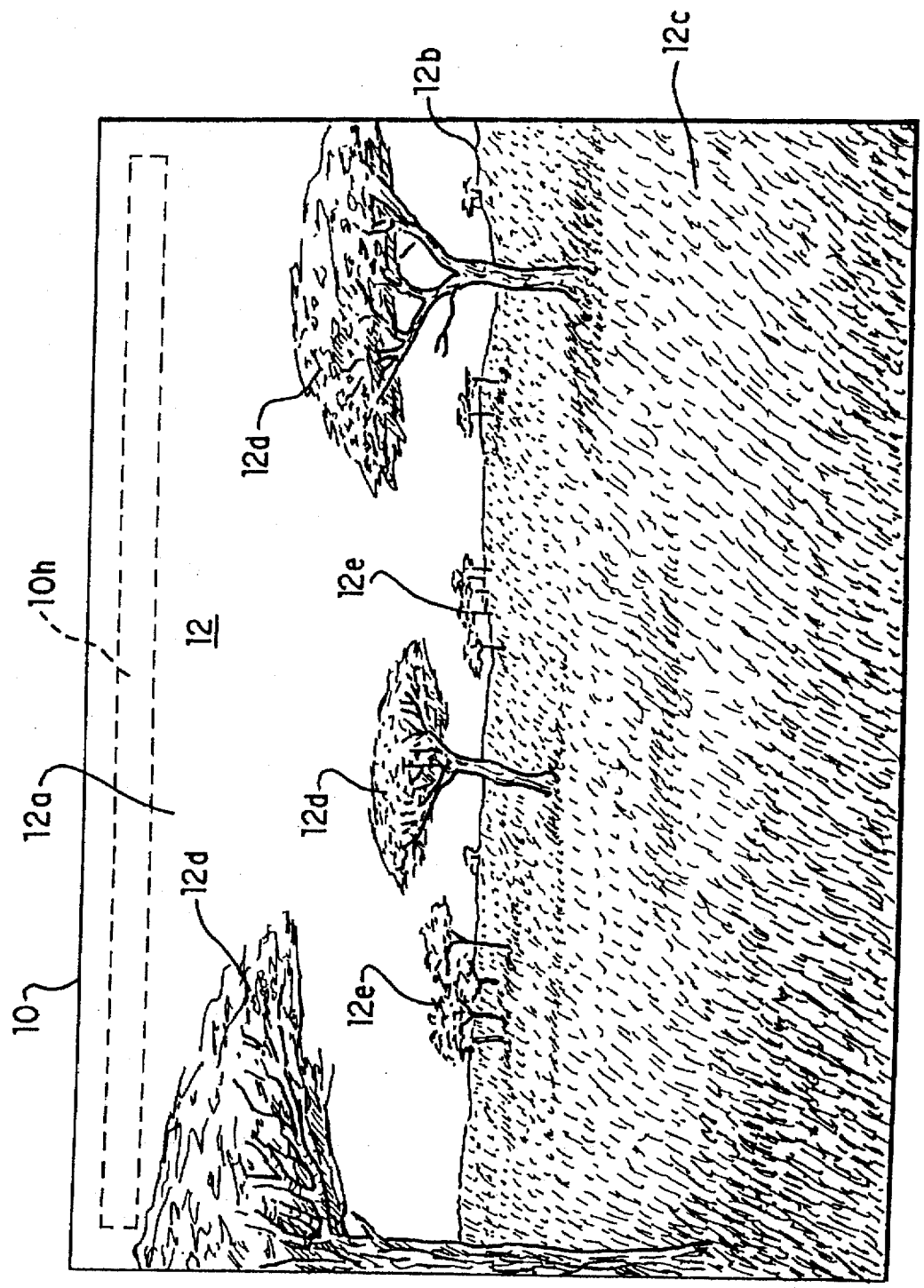
FIG. 2 is a front elevational view of a biophilic landscape image on a flexible fabric display used with the method and apparatus of FIG. 1.

As shown in FIG. 2, preferred biophilic picture 12 depicts a savanna-type landscape scene. Biophilic picture 12 is appropriately selected from a scrutinized set of pictures, and includes a wide, preferably blue, sky portion 12a beginning along and extending above distant horizon line 12b. Horizon line 12b separates sky portion 12a from savanna-type vegetation comprising substantially herbaceous understory of plant life 12c (preferably grasses, sedges and the like) under a relatively open canopy formed by substantially widely spaced trees 12d, and/or tree clusters 12e.

Figure 5:
FIG. 5 is a front elevational view of a roll-up-able and roll-down-able device for displaying a still further spatially open natural landscape imagery including a substantially serene hydric feature.

Although depiction of water is not shown in the preferred embodiment of FIGS. 1 and 2, in the alternative, FIG. 5 shows display device 50 of shade-like material 52m with picture 52 including a spatially open natural landscape and tranquil water body 52f.

To prevent or reduce undesirable stimulation of the imagination or the balance of patient 14, negatively exciting or anxiety producing landscapes are avoided in selecting biophilic picture 12. In addition, distracting display means, such as optically glare-producing video screens are avoided.

As noted previously, according to Ulrich and Wilson, human beings are believed to be genetically pre-disposed to favor views of savanna-type scenes with a particular vegetation physiognomy, such as shown in biophilic picture 12, because the environmental scene shown therein resembles savanna-type landscape conditions under which natural selection pressures promoted evolutionary differentiation of the genus Homo from paleoanthropoids.

Therefore, appropriate standards of selecting landscape scenes with particular vegetation physiognomy are used to narrow the field of the appropriate pictures to choose from.

Figure 3:
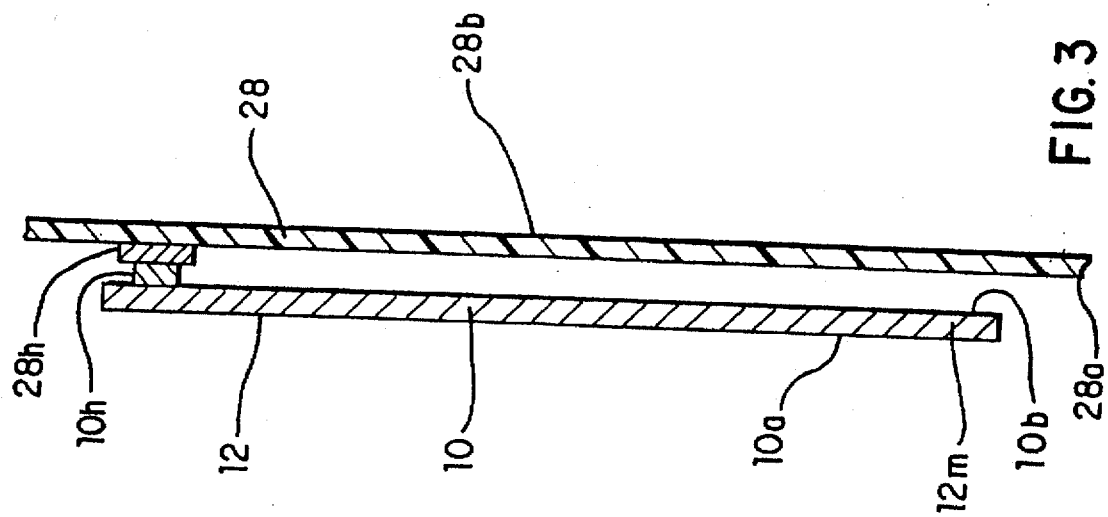
FIG. 3 is a side elevational view in cross-section of the flexible fabric displUmy shown in FIG. 2.

As shown in FIG. 3, display device 10 displays, on front side 10a, biophilic picture 12 printed on fire retardant flexible panel of fabric material 12m. Rear side 10b of display device 10 is attached to curtain 28 by conventional fasteners, such as hoop-and-loop fastener 10h, corresponding to hook-and-loop fastener 28h attached to front side 28a of curtain 28 also having rear side 28b, which curtain 28 can be made of fabric or synthetic resins. Alternatively, fastener snaps pins (not shown) or other fastener devices may be employed to attach a display device to a flexible curtain, such as curtain 28, or another kind of structure, (such as ceiling 81 or curtain 88 in hospital room 96, shown in FIG. 8) or a wall or other like structure.

If a person is convalescing at home without a hospital curtain, the visual display means may include a picture frame, wherein biophilic picture 12 is mountable in the frame, as long as the size of the picture is increased to provide an intimate, proximate setting of the selected picture in the patient's room.

Figure 4:
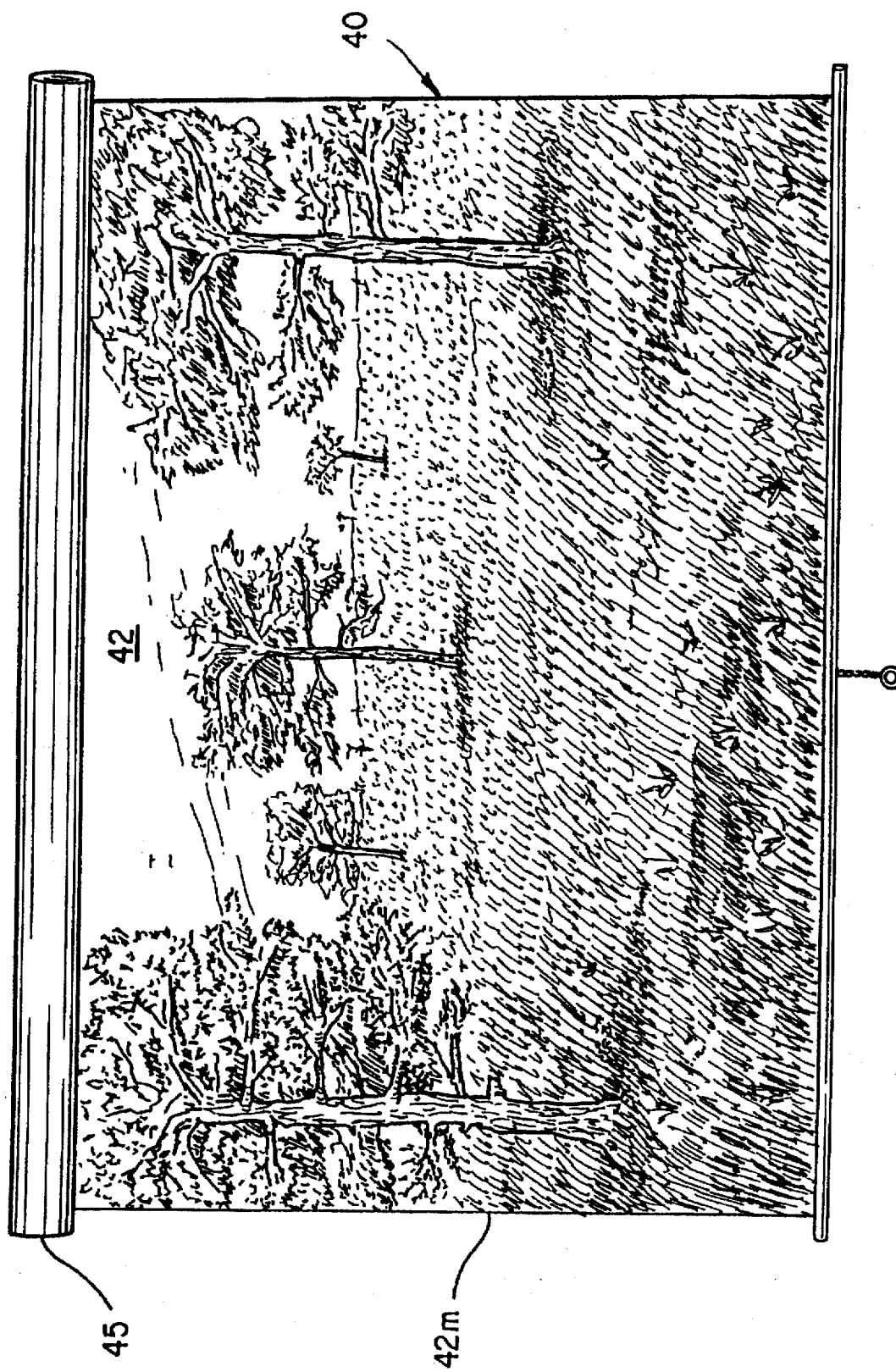
FIG. 4 is a front elevational view of roll-up-able and roll-down-able device for displaying another spatially open natural landscape image.

In the alternative embodiment shown in FIG. 4, display device 40 includes roll-up-able and roll-down-able shade-like material 42m which is substantially rollable about an inner spindle (not shown) within support cylinder 45 wherein spatially open natural landscape picture 42 is adhered to roll-up-able and roll-down-able shade-like material 42m.

In a further alternate display embodiment shown in FIG. 5, display device 50 is also roll-up-able and roll-down-able shade like material 52m, which is substantially rollable about an inner-spindle (not shown) within support cylinder 55, wherein further spatially open, serene natural landscape picture 52, also showing tranquil hydric water body 52f, is displayed on roll-up-able and roll-down-able shade like material 52m.

Figure 6:
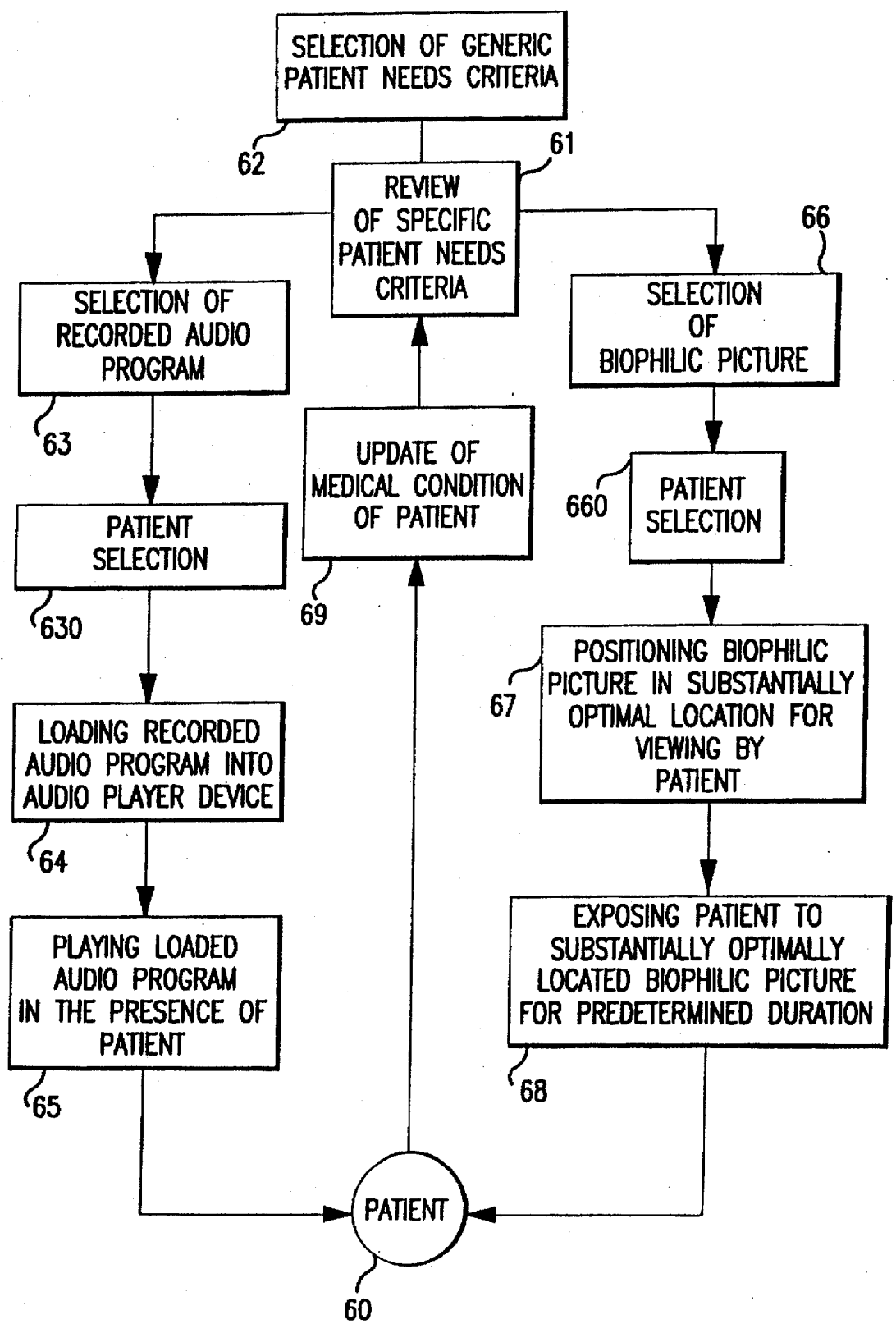
FIG. 6 is a flow chart of an embodiment of the method of the present invention.

FIG. 6 represents a flow chart of the steps of one embodiment of the method of the present invention. In FIG. 6, the medical patient is represented by reference numeral 60. Step 62 represents a care-giver's selection of a distinct, limited set of appropriate visual images or sounds, such as pictures 12, 42, 52, 72 or 82 or sounds 21, 79 or 89 to establish generic patient needs criteria for a variety of patients, such as, for example, patient 60. Step 61 involves a comprehensive review of medical condition of a particular patient, such as, for example, patient 60, to determine the appropriateness of providing one or more spatially open, serene natural landscapes from the distinct set for viewing by patient 60 in an intimate setting. A further selection process includes selecting on parallel tracks the appropriate visual image 66 and related audio program 63 for the patient 60.

In the selection process, step 66 involves selecting a visual image, such as biophilic picture 12 by the care-giver, to select a set of a plurality of images (such as pictures 12, 42, 52, 72 or 82) appropriate for patient 60.

Step 660 of the selection process involves thereafter allowing patient 60 to select which image or images patient 60 wants to view, if any. The exercise of selecting one or more images 12, 42, 52, 72 or 82 by patient 60 is important for bolstering patient 60's feeling of self efficacy, which promotes health and well being, and enhances the recovery process.

Similarly, in step 63 for selection of an appropriate audio program, a set of sounds is first selected by the care-giver, and then in step 630 patient 60 is given the option of which audio program patient 60 wants to hear, or whether or not to hear the audio program at all.

The next steps 64 and/or 67 concern the respective functions of loading the audio program 19 into an audio player device 18 for playing sounds 21, 79 or 89 on speaker 20 to patient 60 and the appropriate positioning of picture 12, 42, 52, 72 or 82 in a substantially optimal location and in a substantially glare-free optical environment for viewing by patient 60.

The respective final steps 65 and/or 68 include playing the loaded audio program 19 to patient 60 through player 18 and speaker 20, in conjunction with exposing patient 60 to picture 12, 42, 52, 72 or 82 for a period of time.

As shown in FIG. 6, the process is periodically renewed, since the medical condition of patient 60 is updated in step 69. Therefore, in step 61 patient 60's needs criteria are periodically reviewed and updated. Moreover, the exercise of choice by patient 60 in the selection steps 630, 660 is updated as well, so that patient can terminate either the playing of audio program 19 and/or the viewing of picture 12, 42, 52, 72 or 82 at will.

In summary, the present invention includes a method of biophilically promoting patient welfare, by exposing a patient to a preferably conveniently mounted, substantially optically glare-free biophilic pictorial landscape image to which human beings are believed to be generally genetically predisposed to viewing favorably, so as to biophilically induce relaxation, reduce stress and/or promote postsurgical recovery. The beneficial effects of providing the landscapes image may be augmented by providing the patient with soothing natural sounds or aromas.

Display materials, having a biophilic pictorial landscape image affixed thereto by substantially glare-free high resolution sublimation printing, can be removably or changeably mounted as a convenient removable flexible and lightweight display member, to a hospital curtain or other structure so as to substantially maximize exposure of a patient to the biophilic image in an intimate, substantially glare-free environment.

It is also important that the pictures be removable, so that the patient can exercise choice in selecting the picture to be viewed, and thereby improve the patient's self efficacy and self esteem.

It is also known that other modifications may be made to the present invention, without departing from the spirit and scope of the invention, as noted in the appended claims.

I claim:

1. Apparatus for promoting patient relaxation and reducing patient stress in a health care setting comprising:

a bedroom containing a bed adapted to support a patient, said room having a flexible curtain forming a movable enclosure around said bed within the room, a visual display member of fire retardant fabric construction to eliminate glare mounted on said flexible curtain and located so that said visual display member is visible at the foot of said bed within the line of vision of said patient, said visual display member having a display on a surface facing said patient, said display being a savanna-type landscape containing imagery designed to create relaxation, reduce stress and expedite recovery of said patient, said display being produced on said fire retardant fabric by a high resolution sublimation printing process resulting in said display and fire retardant fabric being washable and durable to heated washing standards of 160 deg. F. so that any infectious organisms thereon are eradicated, and means for attaching and permitting ready removal of said visual display member to and from said flexible curtain for washing.

2. The apparatus as claimed in claim 1, said apparatus further comprising:

an audio player and a recording of nature-imitating sounds which can be positioned so as to deliver nature-imitating sounds to said patient when said patient is in a reclining position on said bed.

3. The apparatus as claimed in claim 1, said apparatus further comprising a means for delivering aromas of aromatic materials to said patient.

4. The apparatus as claimed in claim 1, wherein said fire retardant fabric is removably attachable to a surface of said flexible curtain by hook-and-loop fasteners, which said hook-and-loop fasteners are parts of said means for attaching.

5. The apparatus as claimed in claim 4, wherein said visual display member includes a roll-up-able and roll-dom-able curtain and wherein said display is imprinted on said curtain.

6. The apparatus as claimed in claim 4, wherein said display includes biophilic landscape imagery suggesting environments in which the evolutionary differentiation of *Homo sapiens* from ancestral paleoanthropoids is believed to have occurred.

7. The apparatus as claimed in claim 6, wherein said biophilic landscape imagery includes imagery of vegetation dominated by a relatively low herbaceous understory and a relatively widely spaced tree canopy.

8. The apparatus as claimed in claim 1, wherein a plurality of different biophilic spatially open natural landscape pictures are provided to the patient for choosing at least one of said pictures.

* * * * *